Figure 1:
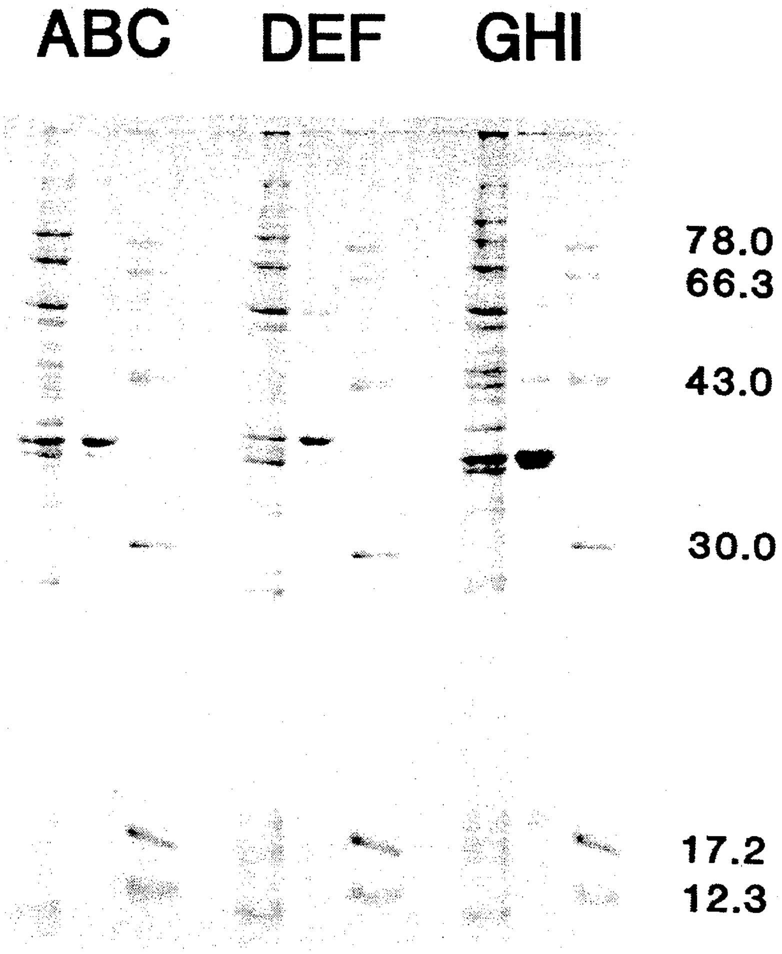

US005240705A

United States Patent [19]

Jacobs

[11] Patent Number: 5,240,705

[45] Date of Patent: Aug. 31, 1993

[54] HAEMOPHILUS PARAGALLINARUM VACCINE

[75] Inventor: Antonius A. C. Jacobs, PS Kessel, Netherlands

[73] Assignee: Akzo NV, Arnhem, Netherlands

[21] Appl. No.: 751,492

[22] Filed: Aug. 29, 1991

[30] Foreign Application Priority Data

Sep. 5, 1990 [EP] European Pat. Off. ........ 90202358.9

[51] Int. Cl.[5] .................... A61K 39/02; A61K 39/102

[52] U.S. Cl. ........................................ 424/88; 424/92

[58] Field of Search ............................ 424/88, 89, 92

[56] References Cited

U.S. PATENT DOCUMENTS

| | | | |
|---|---|---|---|
| 3,876,763 | 4/1975 | Yoshikazu et al. | 424/89 |
| 4,247,539 | 1/1981 | Iritani et al. | 424/92 |
| 4,247,593 | 1/1981 | Iritani et al. | 424/92 |

OTHER PUBLICATIONS

Blackall et al Avian Disease 34: 871-877 Oct. 1990.

Rimlen et al Am. J. Vet. Res. 38: 1581-1590 1977 Abstract only.

Bergey's Manual—p. 568 Haemophilis paragallinarum.

Blackall et al., Avian Diseases, vol. 33, pp. 168-173 (1989).

Bergey's Manual of Systemic Bacteriology, vol. 1, section 5, p. 568, item 15, "Haemophillus paragallinarum" (1987).

*Primary Examiner*—Christine M. Nucker

*Assistant Examiner*—H. Sidberry

*Attorney, Agent, or Firm*—William M. Blackstone

[57] ABSTRACT

The invention is concerned with a vaccine for the protection of poultry against Haemophilus paragallinarum infection.

Chickens vaccinated with a membraneous fraction of H. paragallinarum cells comprising a 38 kD outer-membrane protein are well protected against infection.

12 Claims, 1 Drawing Sheet

HAEMOPHILUS PARAGALLINARUM VACCINE

The present invention is concerned with a vaccine for the protection of poultry against *Haemophilus paragallinarum* infection, *Haemophilus paragallinarum* antigenic material, antibody or antiserum specific for said material and methods for the preparation of a *Haemophilus paragallinarum* vaccine.

*Haemophilus paragallinarum* (*H. paragallinarum*) causes an infection of the upper respiratory tract of chickens called infectious coryza (IC). The most prominent features are involvement of nasal passages and sinuses with a serous to mucoid nasal discharge, facial oedema and conjunctivitis. Infections of the lower respiratory tract, e.g. air sacs and lungs may occur. Although morbidity is high, natural mortality is relatively low. Frequently IC causes an increased number of culls, stunted growth and reduction in egg production resulting in high economic losses. Moreover, IC is usually more severe and prolonged, with resulting increased mortality when complicated with other agents such as fowl pox, Mycoplasma gallisepticum, infectious bronchitis, Pasteurella and infectious laryngotracheitis. Birds recovered from IC often remain reservoirs of infection and serve to maintain the infection in the flock.

At present for the vaccination against IC use is made of whole bacteria. These vaccines can be based on live, preferably attenuated strains, or inactivated virulent strains. However, attenuated live vaccines always involve the risk of inoculating animals with inadequately attenuated pathogenic bacteria which causes disease in the inoculated animal and possible spread of the disease in the flock. In addition attenuated bacteria may revert to a virulent state.

Inactivated vaccines also suffer from a number of drawbacks, e.g. the side-effects which can occur after administration of whole bacteria as a result of the presence of cell wall material, such as lipopoly-saccharide (LPS).

Three distinct serotypes of H. paragallinarum can be distinguished, i.e. serotype A, B or C. Within each serotype a cross-protection based relationship exists between the various *H. paragallinarum* strains. However, birds vaccinated with a *H. paragallinarum* strain belonging to a specific serotype are not protected against infection of *H. paragallinarum* strains belonging to the other serotypes, i.e. immunity is type-specific. Hence, for a sufficient protection against IC preferably birds have to be immunized with a vaccine containing immunogenic material derived from several *H. paragallinarum* serotypes.

Beside the disadvantages of *H. paragallinarum* vaccines based on whole bacteria mentioned above an additional drawback of such a vaccine is that said vaccine containing whole bacteria of the B or C serotype only partially protects the vaccinated birds against subsequent infection with virulent strains of the B or C serotype.

A filamentous haemagglutinin of *H. paragallinarum* serotype A has been isolated and characterized by Iritani et al. (Am.J.Vet.res., 41 (1980), 2114). This filamentous haemagglutinin has protective activity against infection with *H. paragallinarum* serotype A strains.

However, Iritani's method for the isolation of the protective component of *H. paragallinarum* serotype A, i.e. releasing the protective activity from the cells by use of trypsin and isolating the carrier of said protective activity thereafter, is not applicable for serotype C, as according to this isolation procedure no protective component could be isolated from *H. paragallinarum* strains of this serotype.

A new method for the isolation of a protective fraction of *H. paragallinarum* has now been found which can be applied to all serotypes of *H. paragallinarum.*

Said method results in a new purified membraneous fraction of *H. paragallinarum* cells comprising a protein of 38±3 kD, measured in SDS-PAGE (as outlined herein), which is highly protective against *H. paragallinarum* infection in poultry and which is essentially free from cells and filamentous material.

According to the present invention a subunit vaccine, i.e. a vaccine comprising only the necessary and relevant components for protection can be prepared which is derived from a membraneous fraction of *H. paragallinarum* cells comprising the protein of about 38 kD (38 kD protein enriched membraneous fraction). Chickens immunized with such a vaccine are well protected against homologous challenge with a virulent *H. paragallinarum* strain.

An even more complete protection can be achieved if a vaccine derived from an outer-membrane fraction of *H. paragallinarum* cells enriched in a 38 kD outer-membrane protein (OMP) is administered to chickens (38 kD OMP preparation).

This purified 38 kD OMP preparation is essentially free from cells and filamentous material.

The vaccine according to the invention can be further characterized in that the protective activity is sensitive to heat,
sensitive to trypsin treatment, and
sensitive to proteinase-K treatment.

A vaccine according to the invention can also comprise a fragment of said 38 kD OMP which still has immunizing properties, i.e. an immunological equivalent.

The 38 kD protein enriched membraneous fraction can be obtained by culturing *H. paragallinarum* bacteria in medium under conditions promoting expression of the 38 kD OMP, sedimentation of the cell membrane fraction following disruption of *H. paragallinarum* cells, e.g. enzymatically or mechanically (for example by sonication, grinding or french press), whereafter the 38 kD protein enriched membraneous fraction can be isolated, e.g. by centrifuging.

The 38 kD OMP preparation can be isolated by purifying the membraneous fraction mentioned above further into inner and outer membranes, e.g. by density gradient sedimentation or by differential solubilization of the inner membrane by detergents such as Triton X-100 or Sarcosine, followed by centrifuging.

Another method for isolating above-noted fraction or preparation can be applied using antiserum (e.g. monoclonal antibodies) specific for the 38 kD OMP. A membrane extract of *H. paragallinarum* can be applied to a column substrate which contains said specific antiserum for the 38 kD OMP, separating the adsorbed fraction of the extract from the unadsorbed material, and subsequently releasing the adsorbed fraction from the column substrate.

If desired, the 38 kD OMP can be purified to homogenity by methods known in the art, e.g. solubilizing the 38 kD OMP from said 38 kD OMP preparation by extraction with one or more detergents followed by further purification, e.g. by ion exchange or molecular sieve chromatography, under conditions which do not affect the protective properties of the 38 kD OMP.

The purified 38 kD protein enriched fractions can suitably be isolated from *H. paragallinarum* strains from all available serotypes, e.g. serotypes A, B and C or corresponding serotypes known in the art.

The 38 kD OMP to be incorporated into a vaccine according to the invention can be obtained by chemical synthesis, purification from *H. paragallinarum* cells or by recombinant technology.

In the latter case nucleic acid sequences encoding above-mentioned protein or fragments thereof can for example be identified by screening a genomic *H. paragallinarum* DNA bank for individual clones comprising said sequences, e.g. by using a specific reaction with polyclonal or monoclonal antibodies elicited against the 38 kD OMP. The nucleic acid sequences can be ligated to various expression effecting DNA sequences, resulting in a so called recombinant nucleic acid molecule which can be used for the transformation of a suitable host. Such hybrid DNA molecules can for example be derived from plasmids or from nucleic acid sequences present in viruses. The host cell can be of prokaryotic origin, e.g. bacteria or eukaryotic origin such as mammalian cells. The transformed host cells can be used to produce the 38 kD OMP whereafter said protein or 38 kD OMP containing material can be isolated and subsequently incorporated into a vaccine according to the invention.

In another embodiment a live vector vaccine can be prepared comprising non-pathogenic micro-organisms, e.g. viruses or bacteria containing the nucleic acid sequence encoding the 38 kD OMP or fragment thereof cloned into the micro-organisms.

A vaccine according to the invention is derived from a 38 kD protein enriched membraneous fraction or 38 kD OMP preparation of at least one serotype of *H. paragallinarum*, i.e. vaccines comprising said fraction or preparation, or vaccines comprising immunological equivalents of the 38 kD OMP are within the scope of the invention.

Furthermore, a vaccine according to the invention may be in the form of a recombinant DNA vaccine as outlined above.

Preferably, a vaccine according to the present invention contains more than one 38 kD enriched membraneous fraction or 38 kD OMP preparation derived from *H. paragallinarum* strains of different serotypes. The most complete protection against *H. paragallinarum* infection is obtained if a vaccine is administered to birds which contains said membraneous fractions or preparations derived from *H. paragallinarum* strains of serotype A, B and C. Such a trivalent vaccine is a prefered embodiment of the present invention. A trivalent vaccine according to the invention completely protects birds vaccinated with said vaccine against *H. paragallinarum* infection as opposed to vaccines hitherto used based on whole bacteria.

Apart from the *H. paragallinarum* material carrying the protective activity a vaccine according to the invention may also contain an aqueous medium or a water containing suspension, often mixed with other constituents, e.g. in order to increase the activity and/or shelf life. These constituents may be salts, PH buffers, stabilizers (such as skimmed milk or casein hydrolysate), emulsifiers, adjuvants to improve the immune response (e.g. mineral oils, muramyl dipeptide, aluminium hydroxide, saponin, polyanions and amphipatic substances) and preservatives such as thimerosal.

A vaccine according to the invention may additionally contain also immunogenic material derived from other bacteria or viruses infectious to poultry, e.g. Mycoplasma, Newcastle Disease Virus and Infectious Bronchitis Virus.

Preferably the vaccine is administered parenterally, for example subcutaneously or intramuscularly. The vaccine may be administered in this manner both for the active immunization of the vaccinated birds and to laying birds for the passive, immunization of the offspring thereof. In immunized laying birds, the antibodies raised in them will, of course, be introduced into the yolks of their eggs and therefore subsequently in the hatched chicks.

Both the composition of the vaccine and the vaccination system can be varied and depend on the type of animal to be protected, the age and the weight of the animal, the desired duration of the protection, the method of administration and on the question of whether active immunization or passive immunization by means of maternal antibodies is desired. The optimally effective quantity of the active component in the vaccine is approximately 0.1–100 μg per dose for parenteral, e.g. intramuscular or subcutaneous vaccination of poultry. The most preferred dose ranges between 0.3 and 1.0 μg protein.

The above described active immunization against *H. paragallinarum* primarily will be applied as a protective treatment in healthy birds. It goes without saying that birds already infected by *H. paragallinarum* can be treated with antibodies directed against a membraneous fraction or preparation according to the invention.

Antiserum directed against a membrane fraction according to the present invention can be prepared by immunizing birds with an effective amount of said fraction, preferably in the presence of an adjuvant. If desired the animals can be boostered with a second vaccination to elicit an appropriate immune response. Thereafter the animals are bled and antiserum can be prepared.

The antiserum or antibodies can be mixed with a pharmaceutically acceptable carrier.

Polyclonal antiserum specific for the membraneous fraction derived from a *H. paragallinarum* strain of a specific serotype can be prepared by incubating antiserum elicited against said membraneous fraction, with a mixture of membraneous fractions of *H. paragallinarum* strains of the other serotypes. Antibodies not specific for said *H. paragallinarum* membraneous fraction will adsorb to the added *H. paragallinarum* fractions and can thus be separated from the incubation mixture resulting in an antiserum preparation specific for a *H. paragallinarum* membraneous fraction of a certain serotype.

Monoclonal antibodies directed against a membraneous fraction or preparation according to the invention can also be used for the passive immunizing of birds infected with *H. paragallinarum*. Said monoclonal antibodies can be produced by methods known in the art e.g. by immunizing mice with a membraneous fraction according to the invention, immortalizing mouse spleen cells and selecting hybridomas producing useful antibodies.

Above-mentioned antisera and monoclonal antibodies can also be used for the immunological diagnosis of birds infected with *H. paragallinarum* bacteria.

EXAMPLE 1

Purification of *H. paragallinarum* Membrane Fractions and Immunization of Chickens Bacterial strains were streaked out on chocolate agar, incubated for 24 h at 37° C. in an atmosphere in which a candle was allowed to burn out and then cultured in TPB supplemented with 0.01% NADH.

230 ml of a concentrated H-18 (serotype C) cell suspension (containing $4\times10^{10}$ cells per ml of 40 mM PBS +0.01% thimerosal) was ultrasonicated for 6 min. at 4° C. and 100 Watt, using a Branson B12 Sonifier (30 sec. periods of sonication were alternated by 30 sec. of cooling periods). Subsequently, the unbroken cells were spun down (10 min., $5000\times g$) and 20 ml of the supernatant was emulsified in mineral oil water-in-oil adjuvant (W/O). This vaccine is called SUP-USO (C). The remaining 210 ml supernatant was centrifuged for 1 hour at $167{,}000\times g$ in an ultracentrifuge, to purify the total membrane fraction from the soluble fraction.

The membrane pellet (brownish colour) was resuspended in 60 ml 50 mM Tris-HCl, pH 8.0. 10 ml of this suspension was diluted $3\times$ with the same buffer and emulsified in W/O adjuvant. This vaccine is called 38 kD protein enriched membraneous fraction (C). The remaining 50 ml of the suspension was 1:1 mixed with 50 mM Tris-HCl, pH 8.0+2% Sodium-N-Lauroyl sarcosine and incubated for 2 h at room temperature, to solubilize the inner membranes. Subsequently, the mixture was again centrifuged for 1 hour at $167{,}000\times g$ to separate the solubilized inner membranes from outer membranes.

The pellet was suspended in 50 ml 50 mM Tris-HCl, pH 8.0. Part of this suspension was then diluted $3\times$ in the same buffer and emulsified in W/O adjuvant. This vaccine is called 38 kD OMP preparation (C).

The protective rate of the different purified fractions emulsified in W/O adjuvant is shown in Table 1.

Commercial Isabrown chickens were vaccinated once with 0.5 ml of the different vaccines at 10 weeks of age, and homologously challenged four weeks later with *H. paragallinarum* strain H-18 (serotype C). For each vaccine, 6 chickens were used.

TABLE 1

Protection of chickens against *H. paragallinarum* infection by immunization with purified fractions

| vaccine | clinical signs: score[a] | clinical signs: % protection | re-isolation: no. of chickens[b] positive | re-isolation: % protection |
|---|---|---|---|---|
| Control | 17 | 0 | 6 | 0 |
| SUP-USO (C) | 12 | 29 | 4 | 33 |
| 38 kD protein enriched membraneous fraction (C) | 1 | 94 | 1 | 83 |
| 38 kD OMP preparation (C) | 0 | 100 | 0 | 100 |

[a]The score is presented as the total no. of chickens with nasal discharge, from three observations: 24 h, 48 h, and 5 days post-challenge.
[b]Re-isolation from sinus infraorbitalis, 5 days post-challenge (satellite growth).

As is evident from Table 1, the purified membraneous fraction of *H. paragallinarum* and especially the purified 38 kD OMP preparation (C) appeared highly protective, presumably due to an optimal immune response evoked by said fraction.

For the preparation of a monovalent 38 kD OMP preparation (A) vaccine, strain 083 (A) was streaked out on chocolate agar and incubated for 24 hours at 37° C. in an atmosphere in which a candle was allowed to burn out and then cultured in TPB supplemented with 0.01% NADH. After incubation at 37° C. for 24 hours, the cells were spun down and purified 38 kD outer membrane protein preparation (A) was isolated exactly as described for the 38 kD OMP preparation (C).

Isolated OMP (A) was emulsified in W/O adjuvant to make vaccines containing 10 μg/0.5 ml and 1 μg/0.5 ml. To test these vaccines, commercial Isabrown chickens (10 weeks old) were vaccinated intramuscularly (brest) with a single 0.5 ml dose. At day of vaccination and 4 weeks post vaccination blood samples were taken and sera tested for hemagglutination-inhibition (HI) according to standard methods antibodies (indicative for protection).

TABLE 2

HI-A antibody titers in chickens after vaccination with 38 kD OMP preparation (A)

| Vaccine dose | HI-A titer[a] | | | | |
|---|---|---|---|---|---|
| 10 μg | 7 | 5 | 8 | 7 | 10 |
| 1 μg | 5 | 5 | 8 | 7 | 8 |
| control | 0 | 0 | 0 | 0 | 0 |

[a] $^2$log titer, measured 4 weeks after vaccination, 5 chickens per group.

From the results (Table 2) it can be concluded that 100% of the chickens vaccinated with the 10 μg and 1 μg dose, would have been protected (HI-A $>2^0$).

Monovalent 38 kD OMP preparation (B) was prepared exactly as described above except that strain Spross (B) was cultured and used as starting material for the 38 kD OMP preparation isolation.

EXAMPLE 2

Protection of Chickens Immunized with a Trivalent Vaccine

In an experiment a trivalent subunit vaccine (in W/O adjuvant) is prepared and protection is tested against challenge with strains of serotype A, B or C.

Furthermore, a monovalent H-18 (C) vaccine is tested against heterologous challenge with strain 083 (A) and strain Spross (B). The 38 kD OMP preparations of strains 083 (A), Spross (B) and H-18 (C) used for the trivalent subunit vaccine were purified exactly as described in Example 1. The trivalent vaccine contained 100 μg of each protein per dose of 0.5 ml. Monovalent H18 (C) vaccine is identical to the 38 kD OMP preparation vaccine used in Example 1.

Commercial Isabrown chickens were vaccinated once with 0.5 ml of vaccine at 10 weeks of age and challenged four weeks later. For each challenge group 7 chickens were used.

TABLE 3

Protective rate of a trivalent subunit vaccine and a monovalent (type C) subunit vaccine

| challenge strains | (serotype) | vaccine | clinical signs: score[a] | clinical signs: % protection | re-isolation: no. of chickens[b] positive | re-isolation: % protection |
|---|---|---|---|---|---|---|
| 083 | (A) | Control | 18 | 0 | 7 | 0 |
| 083 | (A) | trivalent | 0 | 100 | 0 | 100 |
| 1645 | (A) | Control | 18 | 0 | 7 | 0 |
| 1645 | (A) | trivalent | 0 | 100 | 0 | 100 |
| Spross | (B) | Control | 19 | 0 | 7 | 0 |
| Spross | (B) | trivalent | 0 | 100 | 0 | 100 |
| H-18 | (C) | Control | 20 | 0 | 7 | 0 |
| H-18 | (C) | trivalent | 0 | 100 | 1 | 86 |
| Modesto | (C) | Control | 20 | 0 | 7 | 0 |

TABLE 3-continued

| Protective rate of a trivalent subunit vaccine and a monovalent (type C) subunit vaccine | | | | | | |
|---|---|---|---|---|---|---|
| | | | clinical signs | | re-isolation | |
| challenge strains (serotype) | | vaccine | score[a] | % protection | no. of chickens[b] positive | % protection |
| Modesto | (C) | trivalent | 0 | 100 | 1 | 86 |
| 083 | (A) | monovalent | 21 | 0 | 7 | 0 |
| Spross | (B) | monovalent | 19 | 0 | 7 | 0 |

[a]The score is presented as the total no. of chickens with nasal discharge, from three observations: 24 h, 48 h and 5 days post-challenge.
[b]Re-isolation from sinus infraorbitalis, 5 days post-challenge (satellite growth).

From Table 3 it appears that only homologous protection is induced after vaccination with the monovalent vaccine H-18 (C). The trivalent vaccine protected completely against challenge with all strains tested.

EXAMPLE 3

Characterization of 38 kD Protein Enriched Membraneous Fractions

Purification of the 38 kD protein enriched membraneous fractions and 38 kD OMP preparations derived from serotype A, B and C strains of *H. paragallinarum* (strain 083, strain Spross and strain H-18, respectively) was carried out as described in Example 1.

Purified preparations were run in SDS-PAGE by the method of Laemmli (Nature (1970), 227, 680–685).

The SDS-PAGE with CBB staining of the purified preparations revealed an about 38 kD band as the dominant protein in the OMP preparations. (FIG. 1). FIG. 1 demonstrates the SDS-PAGE gelelectrophoresis profiles of different preparations i.e. SUP-USO and 38 kD OMP preparations, respectively, derived from strain 083 (A) (lanes A–B), Spross (B) (lanes D–E) and H-18 (C) (lanes G–H).
Molecular weight marker proteins are in lanes C, F and I.

| | |
|---|---|
| Cytochrome C, equine | 12.3 kD |
| Myoglobine, equine | 17.2 kD |
| Carbonic anhydrase, bovine | 30.0 kD |
| Ovalbumine, hen egg | 43.0 kD |
| Albumine, bovine serum | 66.3 kD |
| Ovotransferrin, hen egg | 78.0 kD |

In order to determine further characteristics of the protective activity of the 38 kD OMP preparations, these preparations were purified from strain 083 (A), Spross (B) and H-18 (C) as described in Example 1 and subjected to heat treatment and enzymatic digestion (trypsine and proteinase-K). Trypsin splits proteins behind positively charged amino acid residues (i.e. lysin, arginin). Proteinase-K is a strong enzyme and splits most proteins into small peptides. Heating to 100° C., leaves the amino acid chain intact but results in (mostly irreversible) unfolding of tertiary and quaternary structure of most proteins. For the enzymatic digestions 2 mg of protein was incubated with 200 μg of enzyme in 1 ml 40 mM PBS, 1.5 hours at 37° C. Control preparations were treated in the same way except that the enzyme was left out. To obtain heat denatured proteins, 2 mg of protein in 1 ml 40 mM PBS was heated to 100° C. for 10 minutes.

Vaccine compositions were prepared resulting in a O/W emulsion comprising 50 μg protein per 0.5 ml dose and were tested against homologous challenge. Commercial Isabrown chickens (10 weeks old) were vaccinated once and challenged 4 weeks later. For each challenge group 6 chickens were used (Table 4).

From the protection experiments it can be concluded that the protective activity is sensitive to heat and enzymatic treatment, as such treatments result in a strong reduction of the protective capacity for all three serotypes.

TABLE 4

| Effect of enzymatic and heat treatment on protective rate of 38 kD OMP preparations | | | | | | | | | | | | |
|---|---|---|---|---|---|---|---|---|---|---|---|---|
| | Type A challenge | | | | Type B challenge | | | | Type C challenge | | | |
| | clin. signs[a] | | reisolation[b] | | clin. signs[a] | | reisolation[b] | | clin. signs[a] | | reisolation[b] | |
| Vaccine OMP-treatment | score | % protection | no. of chickens positive | % protection | score | % protection | no. of chickens positive | % protection | score | % protection | no. of chickens positive | % protection |
| Control | 18 | 0 | 6 | 0 | 17 | 0 | 6 | 0 | 18 | 0 | 6 | 0 |
| 1.5 h 37° C. | 0 | 100 | 0 | 100 | 9 | 47 | 4 | 33 | 0 | 100 | 0 | 100 |
| 1.5 h 37° C. Trypsin | 15 | 17 | 6 | 0 | 12 | 29 | 5 | 17 | 12 | 33 | 5 | 17 |
| 1.5 h 37° C. Proteinase-K | 17 | 6 | 6 | 0 | 16 | 6 | 6 | 0 | 9 | 50 | 3 | 50 |
| 10 min. 100° C. | 10 | 44 | 5 | 17 | 17 | 0 | 6 | 0 | 17 | 6 | 6 | 0 |

[a]The score is presented as the total no. of chickens with nasal discharge, from three observations: 24 h, 48 h and 5 days post-challenge
[b]Reisolation from sinus infraorbitalis, 5 days post challenge (satellite growth).

I claim:

1. A vaccine for the protection of poultry against *Haemophilus paragallinarum* infection, comprising a membraneous fraction of *Haemophilus paragallinarum* cells comprising a protein of about 38 kD measured in SDS-PAGE, said protein in an immunogenically effective amount, said vaccine being essentially free of *Haemophilus paragallinarum* cells and *Haemophilus paragallinarum* filamentous material, and a pharmaceutically acceptable carrier or diluent.

2. A vaccine according to claim 1, derived from an outer-membrane preparation having the 38 kD protein as a major protein component.

3. A vaccine according to claim 1, derived from membraneous fractions of *Haemophilus paragallinarum* cells of at least two different serotypes.

4. A vaccine according to claim 3, derived from membraneous fractions of *Haemophilus paragallinarum* cells selected from the group consisting of serotypes A, B and C.

5. A vaccine according to claim 1 additionally comprising at least one other microorganism infectious to poultry or immunogenic material thereof.

6. A vaccine according to claim 1, additionally comprising an adjuvant.

7. *Haemophilus paragallinarum* antigenic material, comprising a membraneous fraction of *Haemophilus paragallinarum* cells comprising a protein of about 38 kD measured in SDS-PAGE, said protein, essentially free of cells and filamentous material.

8. Antigenic material according claim 7, comprising an outer-membrane preparation having the 38 kD protein as a major protein component.

9. A method for the preparation of a vaccine according to claim 1, comprising culturing *Haemophilus paragallinarum* bacteria cells in medium, disrupting cultured *Haemophilus paragallinarum* bacteria cells, separating membraneous material therefrom comprising a protein of about 38 kD by centrifugation and mixing said material with an adjuvant to form a preparation with immunizing activity.

10. A method for the protection of poultry against *Haemophilus paragallinarum* infection, comprising administering an immunologically effective amount of the vaccine according to claim 1 to the poultry.

11. An antiserum immunoreactive with the *Haemophilus paragallinarum* antigenic material according to claim 7.

12. A pharmaceutical preparation comprising antiserum according to claim 11 and a pharmaceutically acceptable carrier or diluent.

* * * * *